United States Patent [19]

Starostovic, Jr.

[11] Patent Number: 5,699,274

[45] Date of Patent: Dec. 16, 1997

[54] PANEL PERFORMANCE TEST SYSTEM

[75] Inventor: Edward J. Starostovic, Jr., Stoughton, Wis.

[73] Assignee: Timberco, Inc., Madison, Wis.

[21] Appl. No.: 558,356

[22] Filed: Nov. 16, 1995

[51] Int. Cl.$^6$ ............................. G01N 3/20; G01N 29/00
[52] U.S. Cl. ..................... 364/508; 73/852; 73/849; 73/812; 73/785
[58] Field of Search ......................... 364/508, 552, 364/554; 73/579, 602, 583, 588, 600, 618, 639, 597, 644, 852, 849, 580, 650, 785, 812

[56] References Cited

U.S. PATENT DOCUMENTS

| | | |
|---|---|---|
| 2,439,130 | 4/1948 | Firestone . |
| 3,194,063 | 7/1965 | McKean . |
| 3,423,991 | 1/1969 | Collins . |
| 3,504,532 | 4/1970 | Muenow et al. . |
| 3,512,400 | 5/1970 | Lynnworth . |
| 3,513,690 | 5/1970 | Pellerin et al. . |
| 3,858,437 | 1/1975 | Jarzynski et al. . |
| 3,861,200 | 1/1975 | Dory . |
| 3,888,108 | 6/1975 | Brands . |
| 4,147,064 | 4/1979 | Bond . |
| 4,201,093 | 5/1980 | Logan . |
| 4,213,349 | 7/1980 | Miura . |
| 4,313,348 | 2/1982 | Madsen . |
| 4,338,820 | 7/1982 | Jassby et al. . |
| 4,481,820 | 11/1984 | Thomann . |
| 4,492,117 | 1/1985 | Chubachi . |
| 4,589,288 | 5/1986 | Porter et al. . |
| 4,838,085 | 6/1989 | Pellerin et al. . |
| 4,926,694 | 5/1990 | Crews, Jr. et al. . |
| 4,982,609 | 1/1991 | Talley, III . |
| 5,060,516 | 10/1991 | Lau et al. ............... 73/602 |
| 5,127,271 | 7/1992 | Sato et al. . |
| 5,187,987 | 2/1993 | Anderson et al. . |
| 5,237,870 | 8/1993 | Fry et al. . |

FOREIGN PATENT DOCUMENTS 918286   1/1973   Canada .

OTHER PUBLICATIONS

Voluntary Product Standard PS-2, US. Dept of Commerce, Feb. 1992.

Primary Examiner—Emanuel T. Voeltz
Assistant Examiner—Cuong Nguyen
Attorney, Agent, or Firm—Teresa J. Welch; Stroud, Stroud, Willink, Thompson & Howard

[57] ABSTRACT

The invention is a performance testing system, i.e., performance of a material under a load concentrated in a single area. The system is computerized and automatically applies a load to a panel to be tested, reads and records deflection of the panel without operator involvement, and provides a printed test report.

13 Claims, 12 Drawing Sheets

Date:
Time: 14:52
Control ID: 53

CONCENTRATED LOAD AND DEFLECTION TEST RESULTS

Inspector:  
End Use/Span Rating: SubFloor - 24

Material: OSB  
Thickness: 23/32"

Maximum Deflection Under 200 lbf Load

| | |
|---|---|
| Deflection Load (lbs.): | 201 |
| Actual Deflection (in.): | 0.214 |
| Permitted Maximum Deflection (in.): | 0.250 |

Test Result: Pass

Minimum Ultimate Load

| | |
|---|---|
| Applied Load (lbs.): | 400 |
| Required Minimum Ultimate Load (lbs.): | 400 |

Test Result: Pass

Date:
Time: 14:32
Control ID: 54

CONCENTRATED LOAD AND DEFLECTION TEST RESULTS
ABC Company

Inspector:  
End Use/Span Rating: Roof - 24

Material: OSB  
Thickness: 7/16"

Maximum Deflection Under 200 lbf Load

Deflection Load (lbs.): 200  
    Actual Deflection (in.): 0.407  
    Permitted Maximum Deflection (in.): 0.469

Test Result: | Pass |

Minimum Ultimate Load

Applied Load (lbs.): 386  
    Required Minimum Ultimate Load (lbs.): 400

Test Result: | Fail |

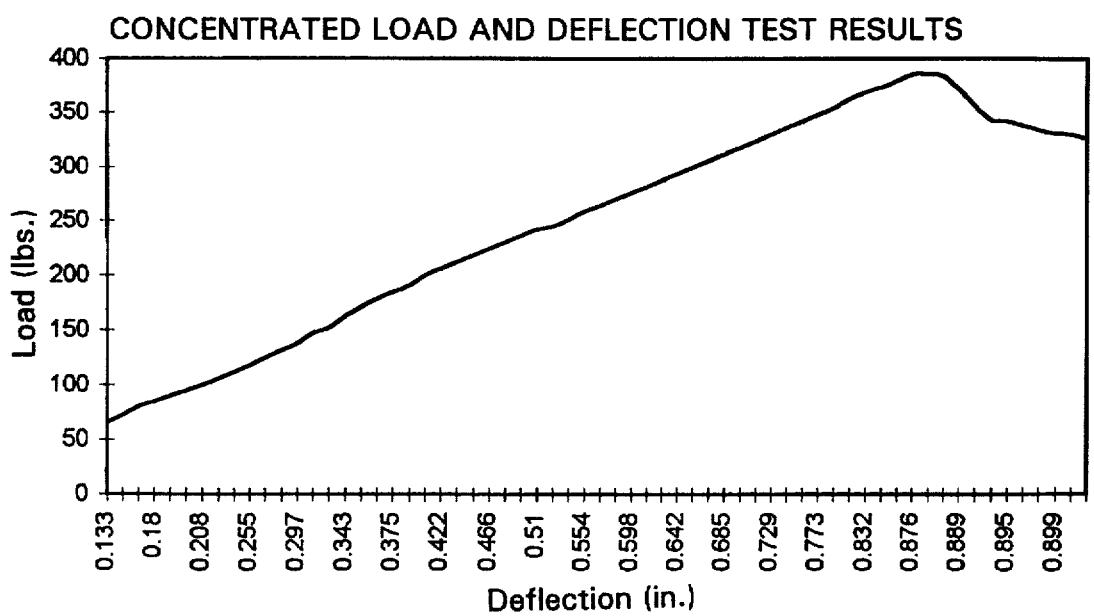

FIG. 15

PANEL PERFORMANCE TEST SYSTEM

TECHNICAL FIELD

This invention relates generally to methods and systems for performance testing of materials and in particular, to a method and system for performance testing of composite materials, for example, wood-based materials such as oriented strand board and plywood.

BACKGROUND OF THE INVENTION

The development of improved composite materials, particularly wood-based materials, such as plywood, oriented strand board, waferboard and the like, has led to increased use of these materials in both engineering and non-engineering applications. Despite such increased use, manufacturers of composite materials often suffer significant quality control problems. Wood-based composite materials can vary relatively widely in strength due to the composite nature of the products and the difficulty in achieving uniform strength in the bonding used to join the components together. Additionally, variations in the feedstocks and other factors make manufacture of uniformly strong and elastic structures from composite elements difficult and costly.

In the industries producing structural-use materials, certain performance standards and performance test methods have been promulgated by various governmental and trade organizations, e.g., the U.S. Department of Commerce and the American Society of Testing and Materials (ASTM), to insure product uniformity. A manufacturer must not only meet such product standards to qualify initially for approval of its products, but must maintain on-going quality, i.e., must conduct a quality assurance program. To maintain quality control, typically, manufacturers must ship many samples weekly from the manufacturing site, e.g., the mill, where the products are made, to remote test centers or laboratories for performance testing. The cost of transportation and testing is significant because a manufacturer may send as many as fifty panels every week to a test site. There has been very little in the way of reliable in-house testing at the manufacturer's site.

One known test for wood-based panels is to take small samples of the panels, e.g., a 1-inch×5-inch coupon, and submit them to a universal test machine in which the sample is stressed to breaking. While such testing is quick and can be accomplished in-house, it has proved unreliable in identifying defects and has mistakenly identified usable product as defective, in the latter case, leading to a significant waste of usable product.

Various patents have attempted to respond to some of the problems of assessment of mechanical properties of composite materials, especially wood products. For example, U.S. Pat. No. 4,589,288 issued to Porter et al. discloses a static bending apparatus for grading wood panels. U.S. Pat. No. 4,838,085 issued to Pellerin et al. discloses methods and an apparatus for nondestructive evaluation of the mechanical properties of composite materials. Other patents that disclose method of inspection and grading of wood products include, Canadian Patent 918286; U.S. Pat. No. 4,313,348 issued to Madsen; U.S. Pat. No. 5,237,870 issued to Fry et al.; U.S. Pat. No. 3,194,063 issued to McKean; U.S. Pat. No. 3,513,690 issued to Pellerin et al.; and U.S. Pat. No. 5,423,991 issued to Collins.

Nondestructive inspection and testing of materials of all sorts are known. For example, U.S. Pat. No. 5,127,271 issued to Sato et al. describes a method of nondestructive inspection of resinous automotive bumper beams, while U.S. Pat. No. 4,982,609 issued to Talley, III discloses a test device for vehicle roof stiffness. Others have disclosed methods of performance testing of materials based on ultrasonic or acoustic techniques. See, e.g., U.S. Pat. No. 3,504,532 issued to Muenow et al.; U.S. Pat. No. 3,512,400 issued to Lynnworth; U.S. Pat. No. 3,858,437 issued to Jarzynski et al.; U.S. Pat. No. 4,201,093 issued to Logan; U.S. Pat. No. 4,338,820 issued to Jassby et al.; U.S. Pat. No. 4,481,820 issued to Thomann; and U.S. Pat. No. 4,492,117 issued to Chubachi. U.S. Pat. No. 2,439,130 issued to Firestone discloses the use of supersonic vibrational waves for inspection of materials qualities. U.S. Pat. No. 3,888,108 issued to Brands discloses a method for impact testing of pavements. U.S. Pat. No. 4,213,349 issued to Miura discloses a method of measuring stiffness of a test piece. U.S. Pat. No. 4,147,064 discloses using stress waves for determining elastic properties of a material.

Most of the known methods for performing certain standards tests are manual methods. For example, to conduct a concentrated load test, it is known to build a frame with beams simulating joists in a building construction. The beams are spaced apart depending upon the end use and span rating of the panel to be tested. A hydraulically-actuated load is applied to the panel at a specified distance from a non-secured edge and the deflection of the panel is measured by placing a dial micrometer under the panel at a position opposite the load and reading the deflection on the micrometer scale.

Despite recognition and study of various aspects of the quality assurance problems with wood-based panels, virtually all of the known methods are manual, labor intensive procedures that can readily lead to error or operator tampering. Accordingly, there is a significant need for methods and apparatus for performance testing of structural elements such as wood panels to provide a reliable quality assurance program for a manufacturer, a system which is fully automatic, eliminates human error and readings, and is useable in-house by the manufacturer.

SUMMARY OF THE INVENTION

The present invention provides a fully automatic structural-use panel performance test system which provides timely and tamper-free quality control testing. The test system is designed for use by a manufacturer on a daily basis to provide daily test results, rather than the weekly results of prior art practices. As such, the system provides reliable monitoring of product quality, heretofore totally unheralded in the prior art. The system is also very cost effective, providing cost savings to the manufacturer. Savings are realized in the elimination of transportation costs, and outside laboratory testing costs. The system in accordance with the present invention is particularly suitable for concentrated load testing, i.e., performance of a material under a load concentrated in a single area. The system automatically applies a load to a panel to be tested, reads and records deflection of the panel without operator involvement, and provides a printed test report.

The foregoing, and other advantages of the present invention, are realized in one aspect thereof in a panel performance testing system which includes a support frame, a load-applying assembly, a linear measurement sensor, and a computer. The support frame supports and, when in operation, clamps a panel to be tested. The panel is dimensioned as a flat, rectangular piece with two major and opposite surfaces. The frame includes (i) a horizontal support section and (ii) a clamping assembly which is supported on the horizontal section. The clamping assembly supports one major surface (i.e., under surface) of the panel along three spaced apart parallel framing members extending substantially across the width of the panel and capable of bearing against the other major surface (i.e., upper surface) of the panel along the same three spaced apart parallel framing members extending substantially across the width of the panel.

The load-applying assembly is supported on the support frame, for applying a substantially linear load to the other surface (i.e., upper surface) of the panel. The load is predetermined depending on the end use and span rating of the panel, as defined hereinafter. The load-applying assembly includes a load cell for developing and transmitting a load-indicating signal corresponding to the applied load. The load is suitably applied via an hydraulically actuated system.

The linear measurement sensor measures the magnitude of deflection of the panel under the applied load. The sensor is suitably a linear displacement transducer for developing and transmitting a deflection-indicating signal corresponding to the deflection of the panel under the applied load.

The computer is operatively connected to the load cell and the transducer, and is configured to receive and process the load-indicating signal and the deflection-indication signal into data records of measured loads and measured deflections to determine whether a measured deflection is greater than a predetermined standard, i.e., maximum permitted, deflection. The computer also automatically applies the load to the panel.

The clamping assembly includes three substantially C-shaped clamps. Each of the clamps has a bottom framing member for supporting the one major surface of the panel and a top portion for clamping against the other major surface of the panel. The top portion of each clamp includes a bottom surface, a first plate beneath the bottom surface, a second plate beneath the first plate and a hose sandwiched between the first plate and bottom surface. The hose is operatively connected to a pneumatic system for admitting and exhausting air to and from the hose. A second plate abuts and is coextensive with the first plate, and is substantially T-shape. The second T-place has a flat, substantially rectangular top member and a perpendicular member downwardly depending lengthwise from the top member. The downwardly depending member has a plurality of protruding, linearly aligned and spaced apart pins. In use, the pins hold fast the panel, simulating nails fastening a panel to joists.

In another aspect, the invention is a load and deflection-measuring system. The system includes an hydraulic subsystem for applying a load to a wood panel to be tested; a load cell, operatively associated with the hydraulic subsystem, for measuring the applied load; a linear displacement transducer for measuring a linear displacement of the panel under the applied load; and a computer for storing and executing a load/deflection measuring program and having a display and at least one user input device, and operatively coupled to the hydraulic subsystem, for controlling the application of the load, and operatively coupled to the load cell and the transducer for recording and processing data relating to the applied load and the deflection. The computer is of the type having a central processing unit, a memory medium and data storage means for storing data records.

The load/deflection measuring program is executed on the computer, for controlling a load/deflection test. As such, the program operatively communicates with the central processing unit, memory and data storage means, for controlling the applied load, receiving a load-indicating signal from the load cell, receiving a deflection-indicating signal from the transducer, processing the deflection-indicating signal into a measured deflection value, comparing the measured displacement value with a standard value, and determining if the measured deflection is greater than the standard value.

In a further aspect, the invention provides a method of testing the performance of wood panel under a concentrated load, said method comprising the computer-assisted steps of (a) storing, in a data table, predetermined standard load and deflection parameters corresponding to end use and span rating of panels, (b) entering end use and span rating data for a panel to be tested, (c) determining a predetermined load for a panel to be tested depending upon the end use and span rating of the panel, and (d) testing the performance of the panel upon application of the load. The testing step includes (i) applying the load to the panel clamped to support surfaces at predetermined span intervals depending upon the span rating of the panel, (ii) measuring the load and developing a load-indicating signal corresponding to the applied load; (iii) measuring the deflection of the panel upon application of the load and developing a deflection-indicating signal corresponding to the measured deflection; (iv) interpreting the load-indicating signal and the deflection-indicating signal to derive measured test data of load and deflection, (v) analyzing the measured test data and a predetermined standard deflection parameter to determine whether the measured deflection of the panel is greater than the standard deflection; (vi) providing a test result; and (vii) printing a report of the test result.

In yet another aspect, the invention is an apparatus for measuring deflection of a material composed of a wood-based panel under application of a predetermined standard load. The apparatus includes first, second and third supports for supporting a panel at spaced apart finite locations, and a load-applying assembly for imparting a load to the panel midway between the supports. The assembly includes a loading disk and an hydraulic means for applying force to the loading disk. The apparatus also includes a load cell operatively connected to the loading disk for measuring the load applied through the loading disk and imparted to the panel, and a transducer operatively connected to the load-applying assembly for measuring the deflection sustained by the panel as a result of the imparted load.

The apparatus further includes a computer for storing and executing a load/deflection measuring program and having a display and at least one user input device, and operatively coupled to the load-applying assembly, the load cell and the transducer. The program records and processes measured data relating to the imparted load and the deflection and compares the measured data to standard maximum data to determine if the measured data exceed the standard maximum data. The program also includes printing a report of test results and a graphical representation of applied load versus measured deflection.

Other advantages and a fuller appreciation of the specific attributes of this invention will be gained upon an examination of the following drawings, detailed description of preferred embodiments, and appended claims. It is expressly understood that the drawings are for the purpose of illustration and description only, and are not intended as a definition of the limits of the invention.

BRIEF DESCRIPTION OF THE DRAWINGS

The preferred exemplary embodiment of the present invention will hereinafter be described in conjunction with the appended drawing wherein like designations refer to like elements throughout and in which:

FIG. 15 is an illustrative test report output of the computer program in accordance with the present invention wherein the panel tested failed the ultimate load test.

DETAILED DESCRIPTION

Figure 1:
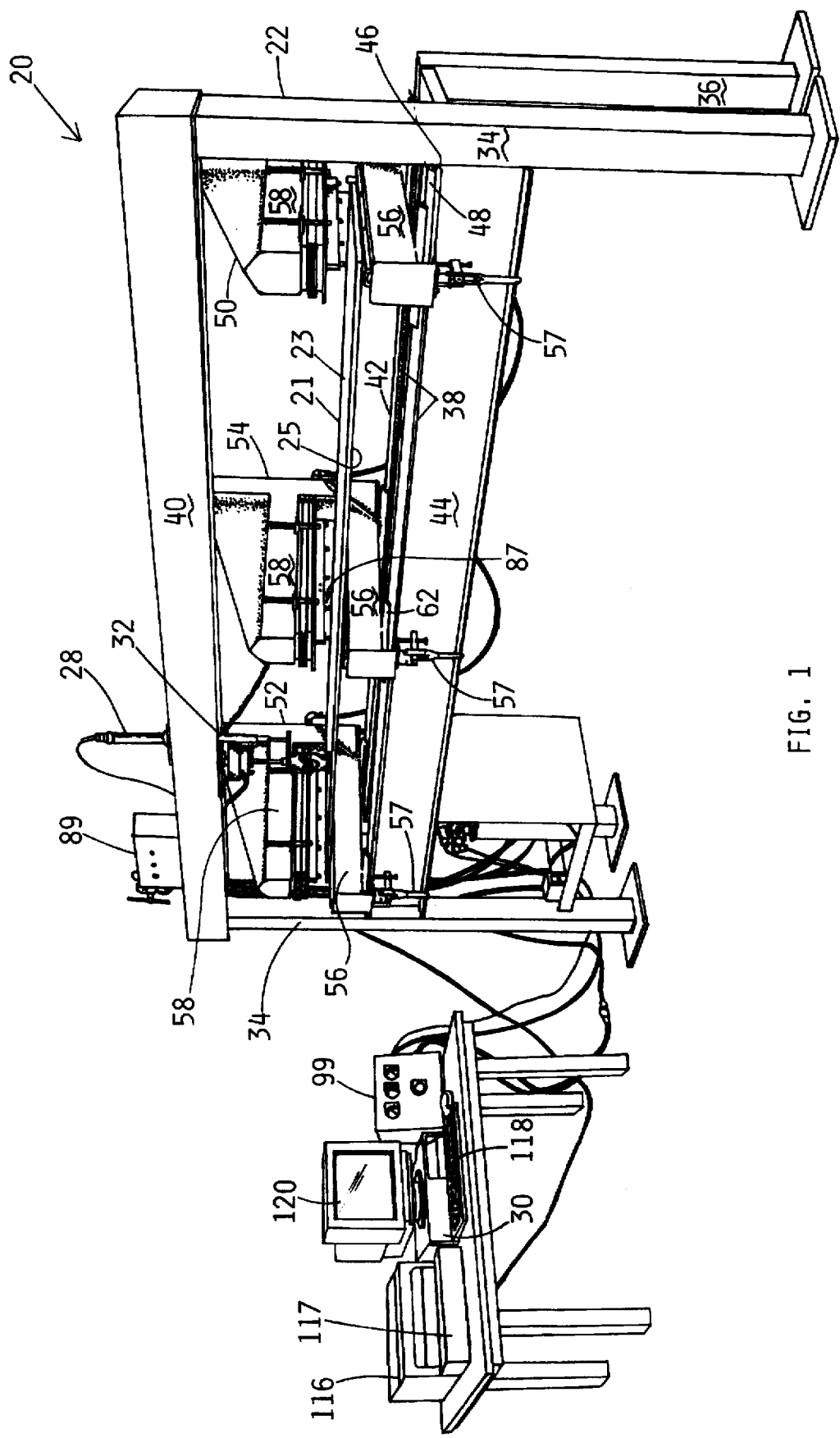
FIG. 1 is a perspective view of an exemplary system constructed in accordance with the present invention.
Figure 2:
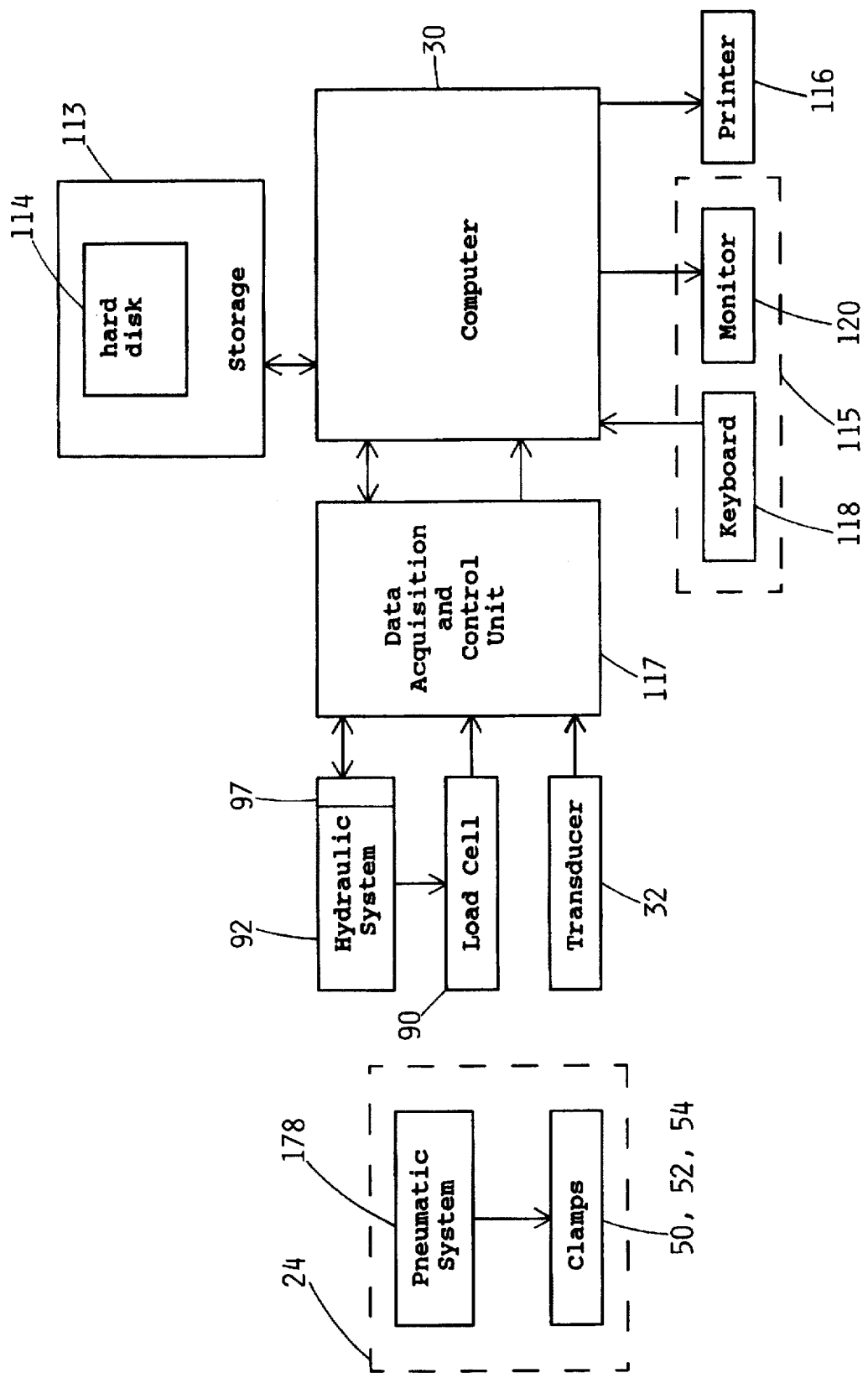
FIG. 2 is a block diagram of the hardware suitable for the exemplary system of the invention shown in FIG. 1.

The present invention relates broadly to quality assurance test procedures. However, the present invention is particularly well-suited for use in performance testing of wood-based products, for example, plywood and oriented strand board (OSB). Accordingly, the present invention will now be described in detail with respect to such endeavors; however, those skilled in the art will appreciate that such a description of the invention is meant to be exemplary only and should not be viewed as limitative on the full scope thereof.

The present invention provides a fully automatic structural-use panel performance test system which provides timely and tamper-free quality control testing. The test system is designed for daily use by a manufacturer to give prompt test results. As such, the system provides the manufacturer the opportunity to react quickly so that necessary process control changes can be made to assure product quality. The system in accordance with the present invention is particularly suitable for a concentrated load testing. The system automatically applies a load to a panel to be tested, reads and records deflection on the panel without operator involvement, and provides printed test report. These attributes are achieved through a novel combination of structural components and physical features.

In the following description of the method of the invention, process steps are carried out at room temperature and atmospheric pressure unless otherwise specified. As used herein, the term "panel" refers to any structural-use material, particularly composite materials such as wood-based panels, e.g., oriented strand board and plywood.

Reference is initially made to FIGS. 1-7 depicting an exemplary performance/quality assurance test apparatus, generally designated as reference numeral 20, in accordance with the present invention. Specifically depicted is an apparatus for testing load deflection for a panel 21, especially a wood-based panel such as oriented strand board (OSB) or plywood. Such panels are typically manufactured in the form of a flat, rectangular piece, i.e., a large sheet, which may be two to four feet in width and four to eight feet in length. Thicknesses range from about ¼ inch to 1.5 inches. As such, panel 21 has a first major surface 23 and a second opposite major surface 25. Apparatus 20 includes a support frame 22, a clamping assembly 24, a load-applying assembly 26, a linear measurement sensor 28, and a computer 30. Frame 22 supports the wood panel to be tested, the assemblies 24 and 26, and linear measurement sensor 28. The clamping assembly 24 holds the panel 21 fast, and as described in detail hereinafter, simulates the nailing of the panel onto a joist. The load-applying assembly 26 is hydraulically actuated and applies a concentrated load to the panel. The linear measurement sensor 28 is in the form of a linear displacement transducer 32 which measures the deflection of the panel sustained under the load.

Figure 3:
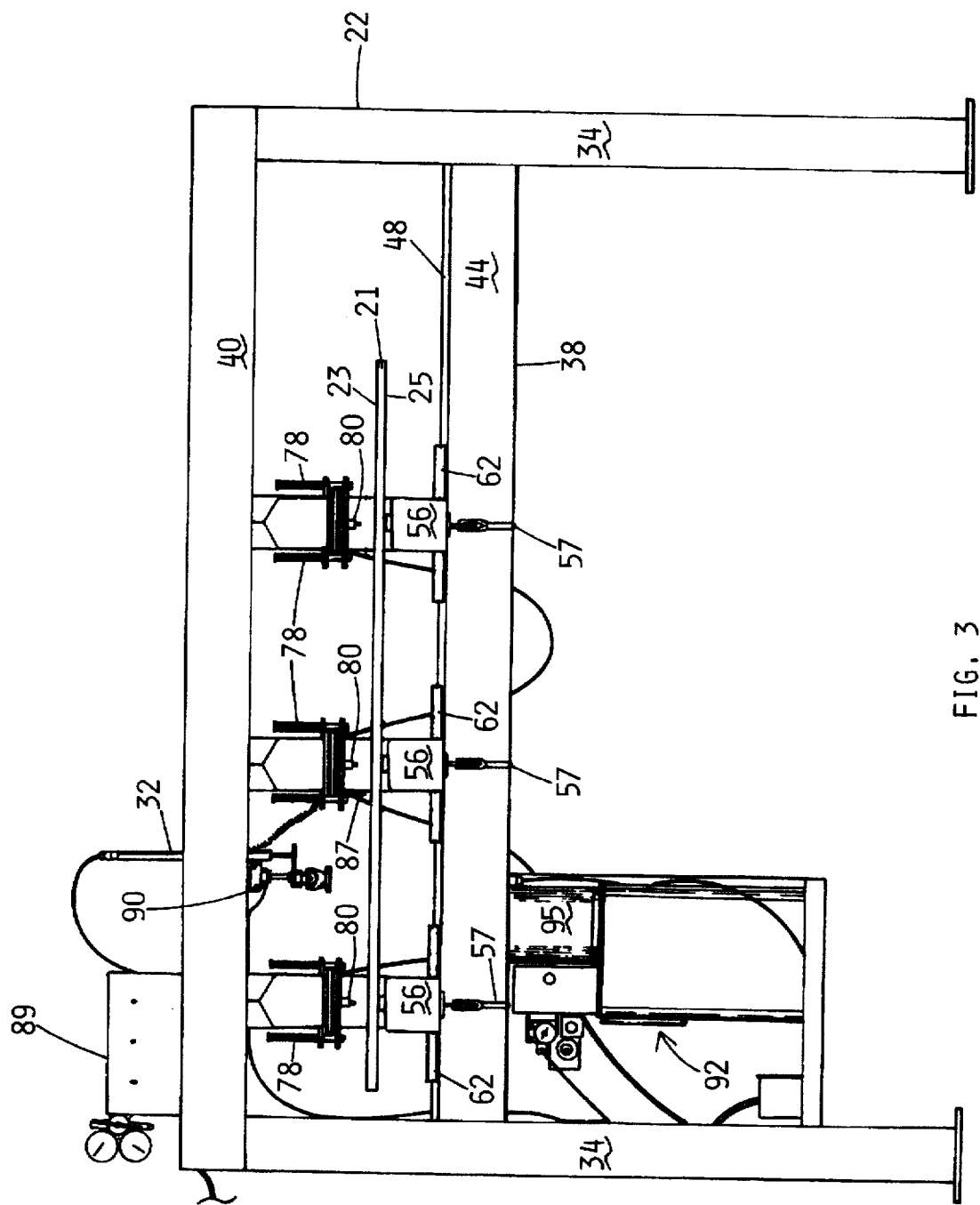
FIG. 3 is a partial front elevational view of the system of FIG. 1 shown supporting of a panel to be tested.

As best seen in FIGS. 1 and 3, the support frame 22 includes a pair of upright, spaced apart front posts or front columns 34, a pair of upright, spaced apart rear posts 36 which are about half the length of front posts 34, a horizontal support section 38 and a cross beam 40 connecting the top ends of upright posts 34. Horizontal support section 38 includes two parallel spaced apart beams 42 and 44. Beam 42 connects the top ends of rear posts 36 and is supported thereby; beam 44 is affixed substantially at the midpoints of front posts 34. The horizontal support section 38 is of sufficient width and length to accommodate panel 21, typically a width of 24 inches. Posts 34 and 36 and cross beam 40 are suitably structural steel posts, and parallel beams 42 and 44 are suitably structural steel I-beams. In overall dimension, the frame 22 is suitably about 9 ft in length and about 3 ft. in width.

Figure 7:
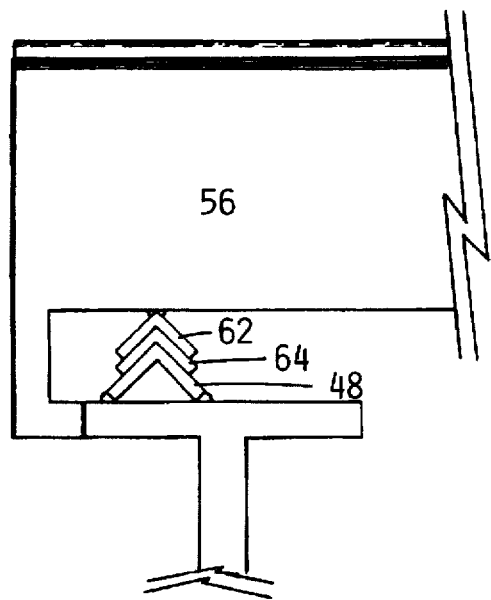
FIG. 7 is an enlarged side view of one of the rails upon which the clamping assembly slides in accordance with the present invention.

Each parallel beams 42 and 44 has a top side 46, e.g., a top of the I-beam, to which is mounted an elongate rail 48 which extends the length of each beam, i.e., rails 48 are parallel and spaced apart as are beams 42 and 44. As best seen in FIG. 7, rails 48 are in the shape of an angled section, i.e., when viewed on end, is an inverted V-shape.

Figure 4:
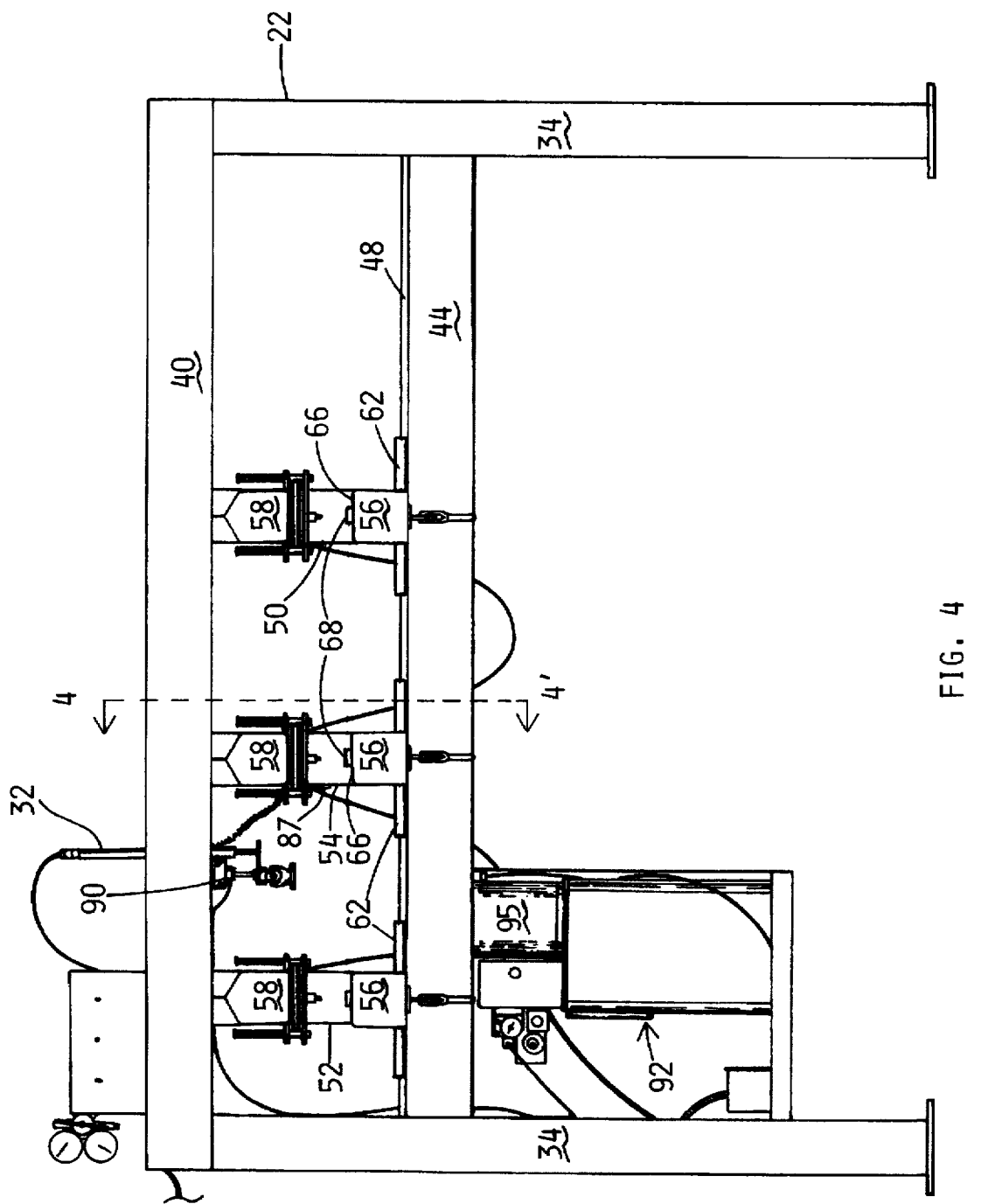
FIG. 4 is a partial front elevational view of the system of FIG. 1 shown without supporting a panel to be tested.
Figure 5:
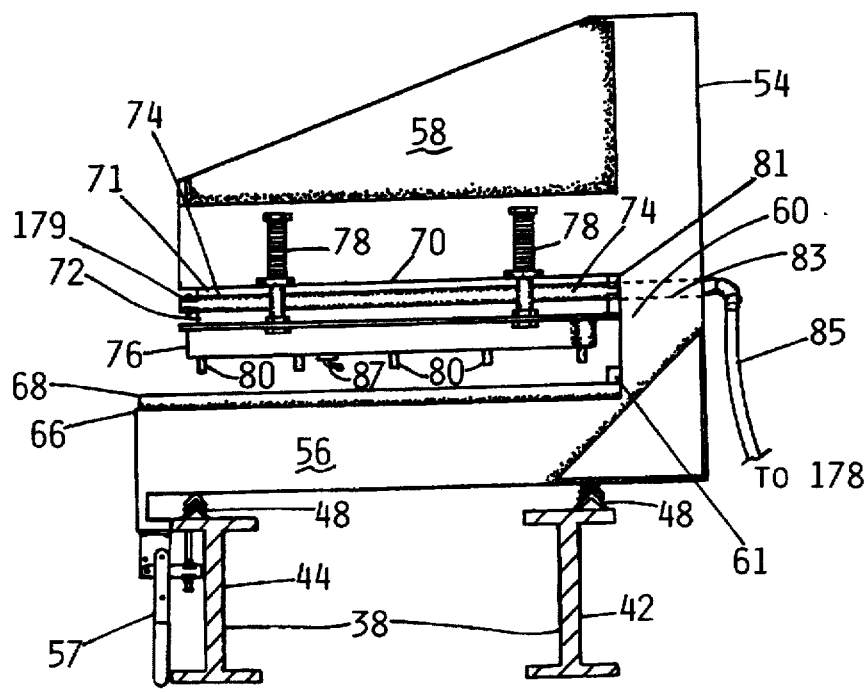
FIG. 5 is a side elevational view of a clamp of the clamping assembly illustrated in FIG. 1 taken along line 4—4' of FIG. 4.
Figure 6:
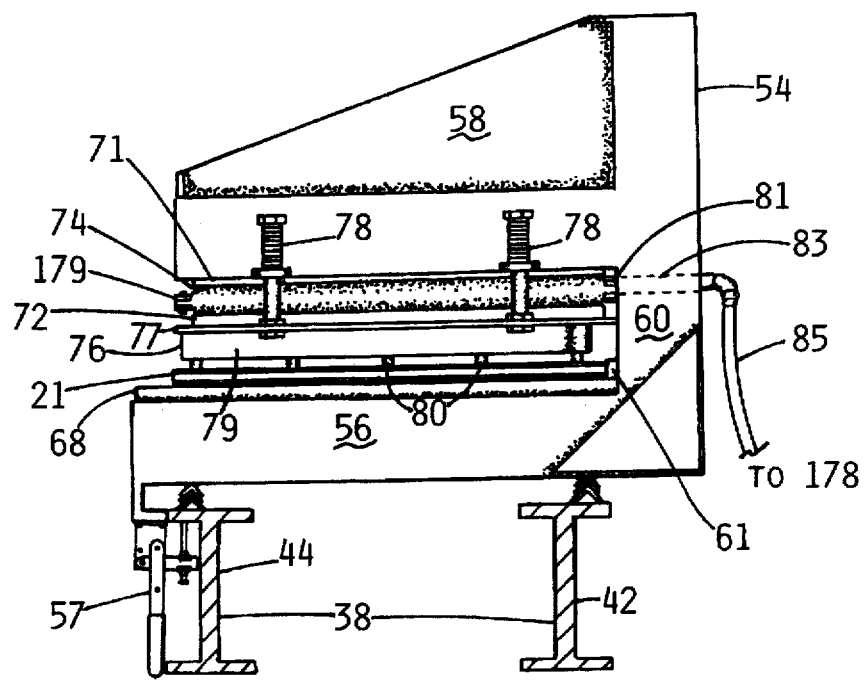
FIG. 6 is a side elevational view of the clamp of the clamping assembly illustrated in FIG. 4, with the clamp supporting and clamping a panel to be tested.

The clamping assembly 24 includes three, substantially C-shaped clamps 50, 52, and 54, respectively. As best seen in FIGS. 4–6, each clamp member 50, 52 and 54 has an elongate, horizontal bottom receiver framing member or receiver jig 56, an elongate horizontal top portion 58 and an upright portion 60 connecting the bottom and top members at one end, thus, forming a substantial C-shape, and suitably made of steel tubing. Receiver jigs 56 support the panel to be tested and include proximate portion 60, a panel stop 61, against which a back edge (i.e., minor edge) of panel 21 rests. Jigs 56 are movably mounted on rails 48 which extend longitudinally beams 42 and 44, and can be clamped to beam 44 via jig clamps 57. Each jig 56 has inverted V-shaped portions 62 which are complementary in shape to each rail 48. Each inverted V-shaped portion 62 has a coextensive pad 64 made of a nonstick polymeric material, e.g., Teflon™.

Thus, clamps 50, 52 and 54 suitably slide along rails 48 and can be adjusted to predetermined spaced apart positions from each other.

Each jig 56 further has a top face 66 upon which a support 68 is mounted longitudinally and affixed. Support 68 is substantially in the form of an elongate inverted U-shape. In performance testing wood panels, support 68 is substantially rectangular in shape with a width of about 1.5 inches, simulating a joist. Panel 21 is supported on the three supports 68 of jigs 56.

Top portion 58 of each clamp member 50, 52 and 54 has a bottom face 70. Beneath and coextensive to face 70 is a first moveable plate 72 and a hose 74 sandwiched therebetween. A substantially T-shaped plate 76 abuts against plate 72, and plates 72 and 76 and hose 74 are held against face 70 via a plurality of springs 78, connecting plate 76 to face 70. T-plate 76 has a flat, substantially rectangular top member 77 and a downwardly depending perpendicular member 79 running the length of T-plate 76. Member 79 has downwardly protruding cylindrical pins 80, linearly spaced apart along the length of member 77. These cylindrical pins 80 when pressed against panel 21 simulate fasteners, e.g., nails, that would be in place in actual environmental use of the panel. Preferably, the cylindrical pins 80 are 6 in. on-center pins that simulate 8-penny nail heads. Hose 74 is clamped at one end by a clamp 179 and connected at the other end with a tubing 81 through a port 83 in the back of top portion 58, via a line 85 to a pneumatic system 178, i.e., to a source of pressurized air (not shown), in a manner well-known in the art. The air pressure is regulated by an air pressure regulator as is well-known in the art. Such a regulator is shown as reference numeral 89 in FIGS. 1 and 3. Hose 74 can be inflated and deflated by admitting and exhausting pressurized air into hose 74 schematically shown in FIG. 6. It is noted that an additional plate 71, positioned directly beneath face 70 is optional depending on the thickness of the panel being tested.

As best seen in FIGS. 5 and 6, when hose 74 is inflated, T-plate 76 moves downward and pins 80 press and hold panel 21. A microswitch 87 controls the penetration of pins 80 into panel 21 to ⅛ inch. Microswitch 87 is suitably a well-known roller type actuator, e.g., stock no. 6X285 available from Grainger of Madison, Wis. Microswitch 87 is positioned on middle clamp 52 and extends somewhat below T-plate 76 and is operatively connected to the air regulator 89. When microswitch 87 is tripped, i.e., when the roller or wheel of microswitch 87 touches panel 21, the switch closes the air flow to the hose 74 in a well-known manner. Hose 74 is suitably a 2.5-inch diameter firehose, e.g., hose #1P957 from Grainger of Madison, Wis.

Figure 8:
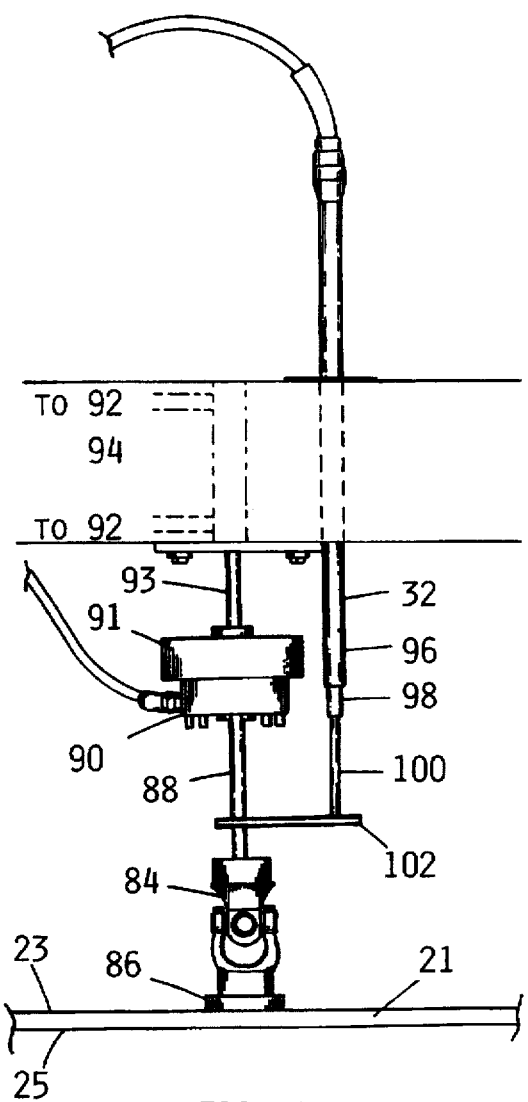
FIG. 8 is a front view of the load-applying assembly and linear displacement transducer suitable for use in accordance with the present invention.

As best seen in FIG. 8, the load-applying assembly 26 includes a universal joint 84 fitted with a flat plate or loading disk 86, and a rod 88 connected to a load cell 90. Load cell 90 is mounted on a load cell plate 91 to which is applied a load which is suitably provided by an hydraulic system 92, in a manner well-known in the art, for example, an hydraulic ram 93 connected to an hydraulic cylinder 94 which in turn is connected to an hydraulic pump 95. The load is applied via loading disk 86 to panel 21, i.e., by controlling actuation of pump 95 through hydraulic cylinder 94 to ram 93. A load cell measures the applied load in a manner well-known in the art. A load cell such as the one described herein is commercially available from Interface, Inc. of Scottsdale, Ariz., e.g., model #1210AF. Pump 95 is operatively connected to computer 30 via a proportional relief valve 97, e.g., an electro-hydraulic proportional pilot relief valve available as model # EPR-GO1-2 from Nachi America to control actuation thereof. It is noted that a manual control 99 for the hydraulic system can also be included in system 20.

As also best seen in FIG. 8, the transducer 32 has an outer cylindrical case 96 fastened to a steel channel inside cross beam 40. As seen, for example, in schematic view in FIG. 8, the case 96 includes a core 98. The lower end of the core 98 is threaded to accept a sensing shaft 100 which is substantially aligned on the vertical plane of symmetry. The lower end of the sensing shaft 100 contacts a measuring plate 102 which in turn connects to rod 88 of load-applying assembly 26. Such transducers are commercially available from Sensotek of Columbus, Ohio, e.g., model DLF DC-DC Long Stroke LVDT. The operation of such transducers, abbreviated LVDT, is known in the art and described in *Sensors And Analyzer Handbook* by H. N. Norton, Prentice-Hall, Inc. (1988) pp. 93–96, incorporated herein by reference.

As predetermined loads are slowly applied to panel 21, the load cell 90 measures the magnitude of the load, typically in pounds applied to panel 21, while transducer 32 records the downward linear travel of the transducer measuring plate 102 corresponding to the deflection of panel 21. Loads are typically delivered to produce deflection at a rate of 0.2 inch/min. (about 200 lbs/min.) Predetermined loads are established in accordance with the end use and span rating of the panel to be tested. For example, wood-based panels such as OSB or plywood, the end use may be roofing, subfloor and single floor panels, sometimes called sheathing. Span ratings, i.e., the distance between joists to which the panel is fastened, range from 16 inches to 60 inches. Load and deflection standards, e.g., ultimate loads (i.e., 400, 550 or 700 lb loads that the panel must withstand without breaking) and maximum deflections at 200 lbs load, are established by the United States Department of Commerce and found is in Voluntary Product Standard PS-2, which is incorporated herein by reference and available from Timberco, Inc. of Madison, Wis. Load cell 90 and transducer 32 are operatively connected via cable to computer 30 so that load and corresponding deflection are measured, i.e., a load/deflection curve is recorded for panel 21 being tested.

Figure 9:
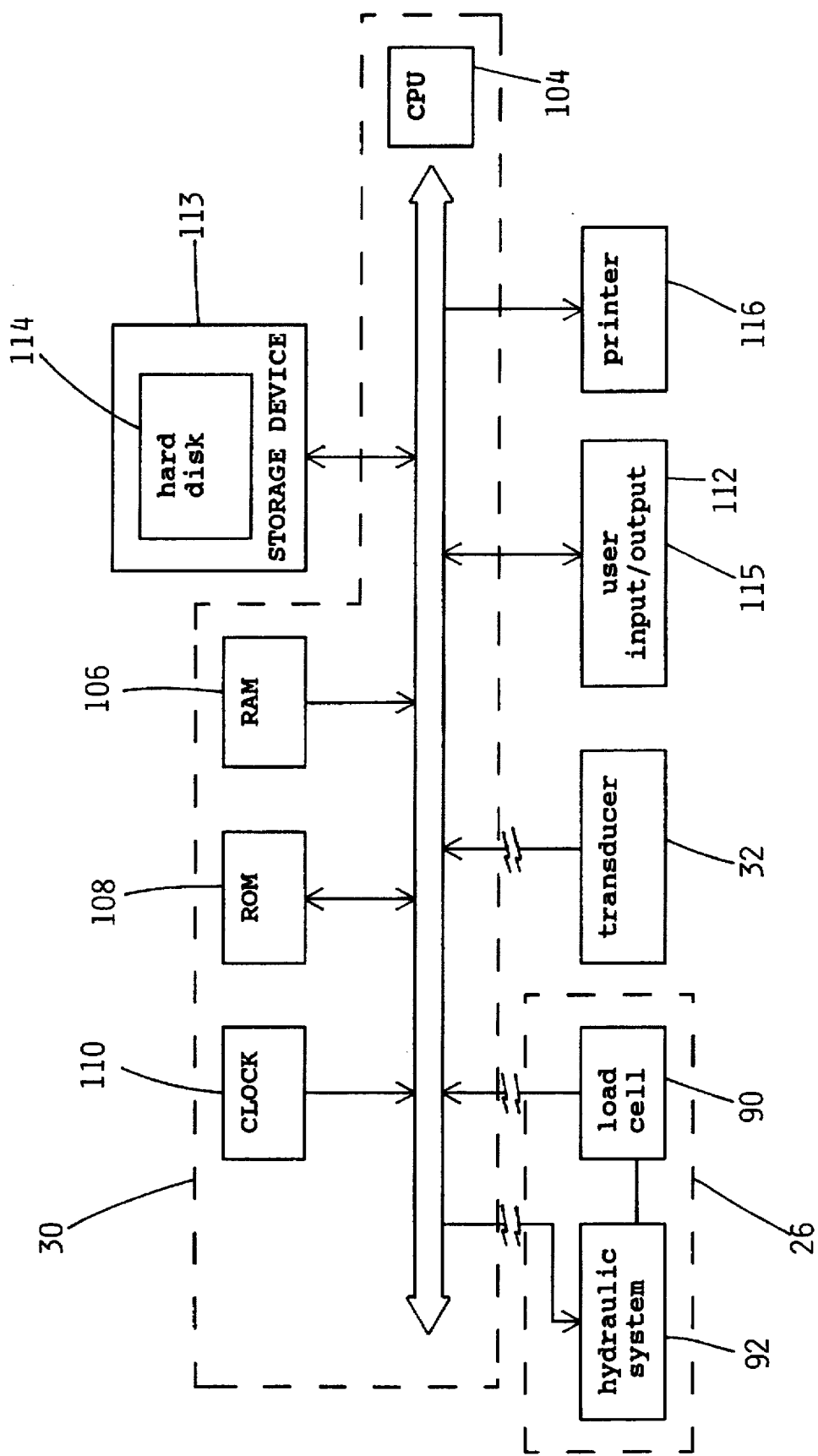
FIG. 9 is a block diagram of the computer system that may be employed in accordance with the present invention.
Figure 10:
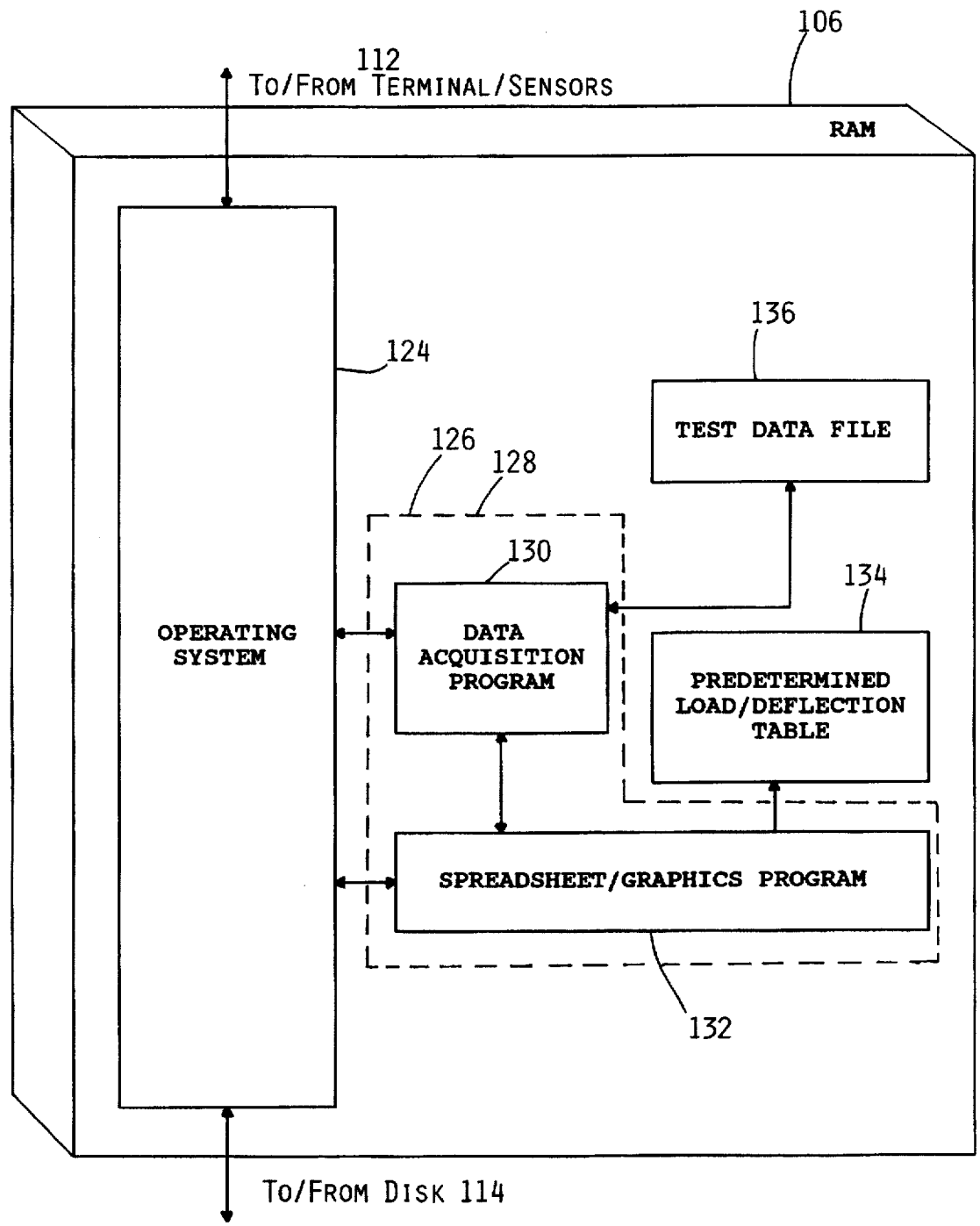
FIG. 10 is a block diagram of the operation of the RAM of FIG. 8 in accordance with the present invention.

Reference is now made to FIGS. 8 and 9 wherein the hardware and software components of computer 30 of the system 20 in accordance with the present invention are depicted in block diagram. The hardware of computer 30 includes a central processing unit (CPU) 104, a random access memory (RAM) 106, a read only memory (ROM) 108, and a clock 110. Computer 30 is also operatively connected to a user input/output device 115, i.e., terminal 112, storage devices 113, e.g., hard disk 114, a printer 116 and a data acquisition and control unit 117. Terminal 112 includes a keyboard 118 and a monitor 120, such as a SVGA monitor. Additionally, computer 30 is operatively connected, i.e., electrically connected, with hydraulic system 92, load cell 90 and transducer 32. The hardware is pictorially represented in FIG. 1. It is evident that the computer is a standard off-the-shelf item having the conventional components, e.g., an IBM compatible computer with 486/66 mHz microprocessor and 8 MB RAM. Unit 117 is an amplifier, D/A converter and interface unit which receives, conditions, converts and passes signals from the load cell, hydraulic system via the proportional relief valve, and the transducer to the computer 30 to CPU 104 where they are acted upon by software portion 126 of system 20 fetched from RAM 106 and necessary information for system operation from ROM 108. Such units are available commercially, e.g., Sciemetric Series 7000 Data Acquisition and Control units.

As seen in FIG. 9, RAM 106 contains a conventional operating system 124, e.g., MS-DOS with a Windows™ environment, both commercially available from Microsoft, Inc., including a system program for loading the software portion 126 of the system in accordance with the present invention into the computer. The software portion 126 of the system is suitably stored in the secondary storage medium, e.g., hard disk 114, for reading by the computer in the conventional fashion. Software 126 includes a load/ deflection program 128. The software portion 126 of the system 20 in effect reconfigures the computer to perform a number of functions, detailed hereinafter.

Program 128 suitably includes a data acquisition program 130 such as WinGen™ available from Sciemetric Instruments of Nephean, Ontario, Canada, and a spreadsheet/ graphics program 132 such as Microsoft Excel™ available from Microsoft, Inc. In a preferred embodiment, WinGen™ operates as a macro in the Excel™ environment. Software portion 126 further includes a data table 134 of data records of established standards which include, for example, for wood-based panels, end use/span rating, ultimate load, and maximum permitted deflection at 200 lbs for panels to be tested.

The data acquisition program 130, responsive to data entry respecting the panel to be tested, controls the hydraulic system and application of the load to the panel, and permits signals to be input into the computer from sensors, i.e., load cell 90 and transducer 32, and stores the signals as measured test data records in a test data text file 136 of measured test data. The measured test data are then processed by the program 132 to provide a graphic representation of measured load versus measured deflection, which can be displayed on monitor 120 or provided as a hard copy via printer 116.

Figure 14:
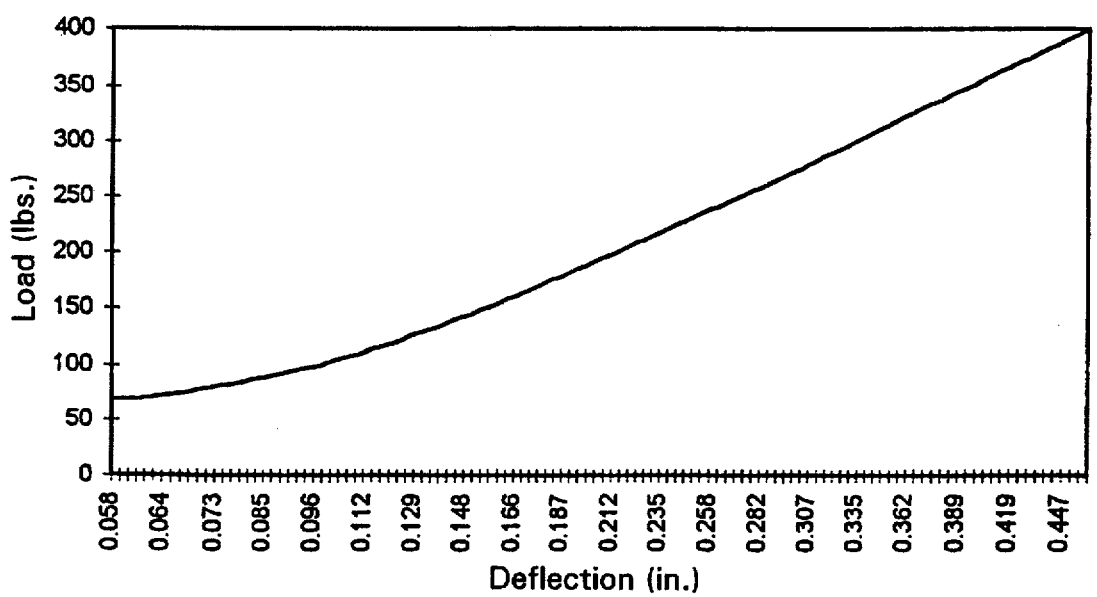
FIG. 14 is an illustrative test result report output of the computer program in accordance with the present invention.

The program 132 also generates in tabular summary report form of the deflection load, the actual deflection, the permitted maximum deflection and the test result, e.g., pass or fail, as shown in FIG. 14.

Figures 11, 12:
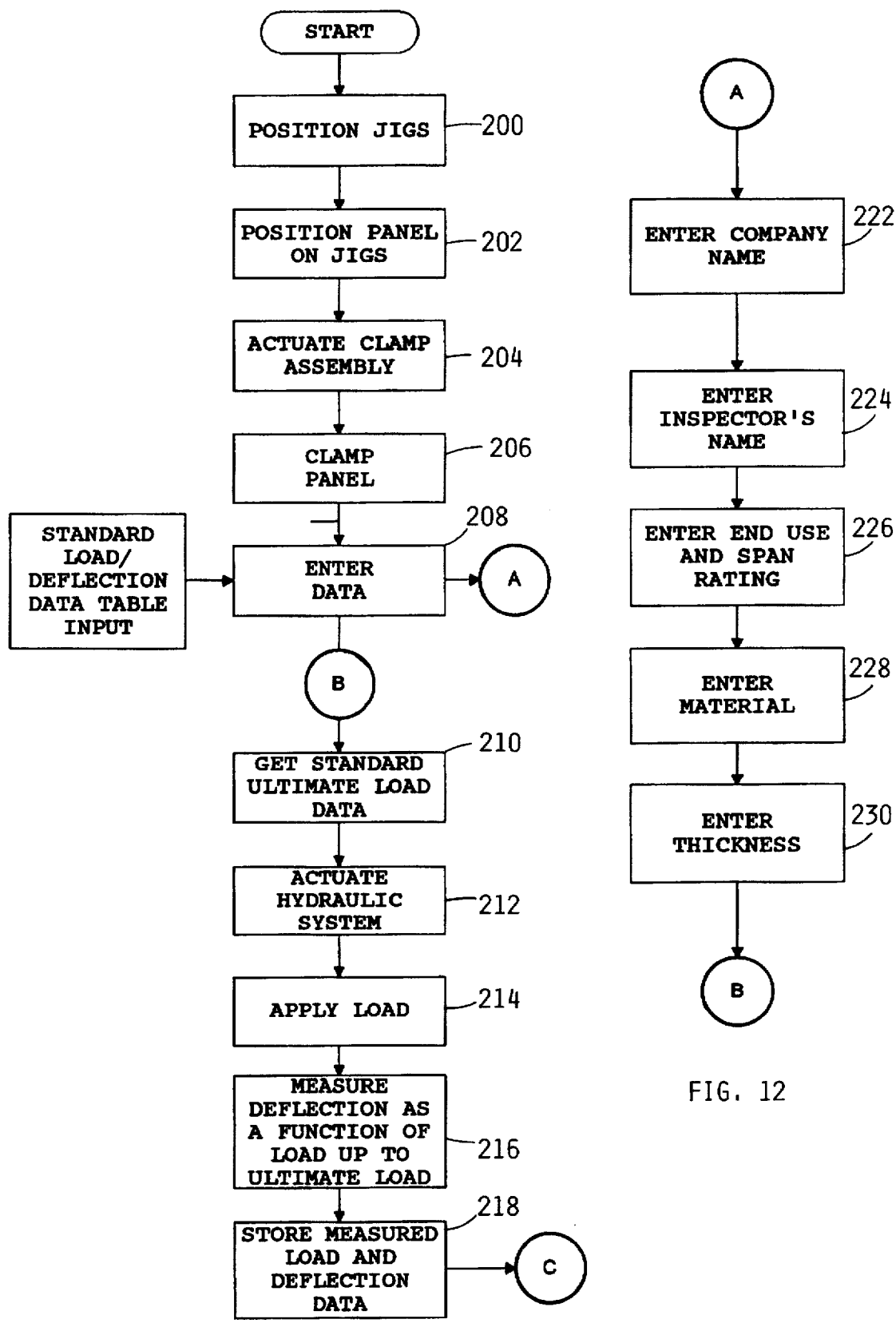
FIG. 11 is a flowchart illustrating the testing in accordance with the present invention including a program for the computer in the system of FIG. 1.
FIG. 12 is a flowchart of the data entry logic of the computer program in accordance with the present invention.
Figure 13:
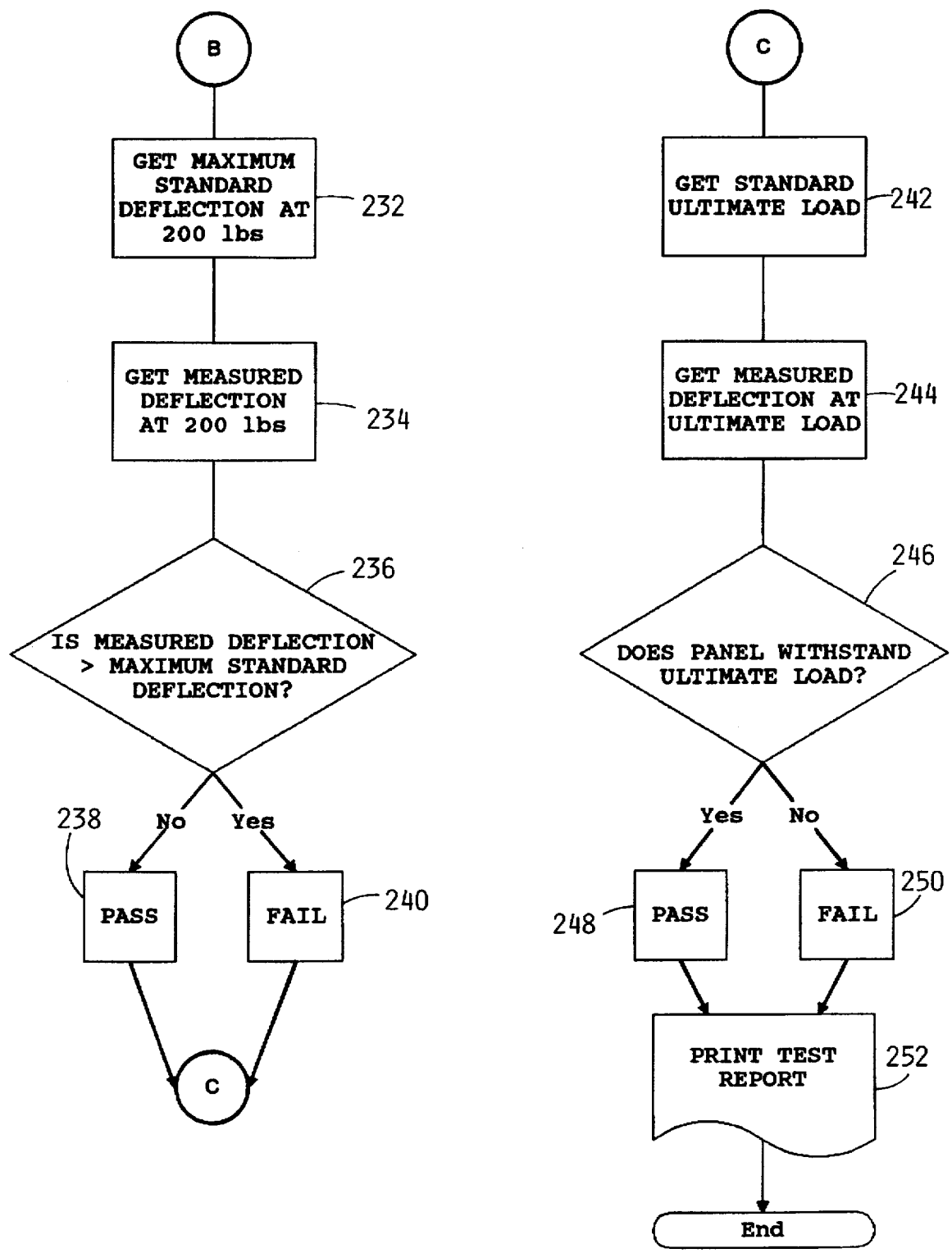
FIG. 13 is a flowchart of the load deflection test logic of the computer program in accordance with the present invention.

Reference is now made to FIGS. 11-13, wherein flowcharts illustrate the logical steps involved in testing a panel in accordance with the present invention. As seen in FIG. 11, to test a panel in accordance with system 20, the overall system begins at step 200 with positioning of the jigs, i.e., clamps 50, 52 and 54 are spaced apart depending on the end use of the panel 21 and the span rating, e.g., roofing panel rated 16 will be placed on horizontal section 30 with the clamps 50, 52 and 54 spaced 16 inches apart. System 20 can handle sheets up to 24 in wide and up to 96 in long. The clamps can be readily spaced to all span ratings from 16 in to 48 in. At step 202, panel 21 to be tested is set horizontally on support section 38 to rest on jigs 56 and against a panel stop 61. At step 204, the clamp assembly 24 is actuated via air regulator 89 to admit air through line into hose 74, and at step 206, panel 21 is clamped into test position as hose 74 expands due to the influx of air and presses T-plate 76 downward with cylindrical pins 80 pressing and holding panel 21.

At step 208, data regarding the panel to be tested is entered as detailed further hereinafter. At step 210, performance standard load data, i.e., ultimate load, is selected from data table 134 according to the panel to be tested, and at step 212, the hydraulic system is actuated and loading disk 86 is placed on panel 21. In turn, at step 214, the predetermined load is applied through loading disk 86 to the panel 21. At step 216, the deflection under the load is measured, more properly the deflection is measured as a function of the load as the load is increased to a predetermined standard ultimate load. At step 218, the load/deflection test data are stored in data file 136.

Once the ultimate load has been applied, hose 74 is deflated by throwing a release switch to release the air from hose 74, and hose 74, plate 72 and T-plate 76 are again pressed against the face 70 of top portion 58 via springing action of springs 78.

Load and deflection test data are received by the computer via a load indicating signal from the load cell and a deflection indicating signal from the transducer, respectively. As described previously, the computer is also programmed to actuate the hydraulic system to apply the predetermined load.

As seen in FIG. 11, data entry step 208 includes several steps. At step 207, the load and deflection program in accordance with the present invention is selected. A data entry screen appears on the monitor and at step 222, the company/manufacturer name is entered, and at step 224, the inspector's name is entered. At step 226, the end use and span rating of the panel to be tested is entered. Optionally, this entry is simply selected from a list of end uses and ratings, by highlighting the desired entry. At step 228, the material description is entered or selected from a list, e.g., plywood or OSB. At step 230, the thickness of the panel is entered, typically in inches. The computer then commences the test by looking up the predetermined loads in the lookup data table 134, actuating the hydraulic system to apply the appropriate load, actuating the transducer to read the deflection, and receiving the deflection indicating signal from the transducer, as described hereinbefore. At the end of the test, i.e., once the ultimate load has been applied, the program deactuates the hydraulic system, and a report, as shown in FIG. 14, is printed.

Testing of the panel is reported in two ways—the concentrated load test and the ultimate load test. Suitable logic for the concentrated load test is illustrated in FIG. 13. At step 232, maximum permitted deflection at 200 lbs. is retrieved from the performance standard data table 134; at step, 234, the measured deflection at 200 lbs. is retrieved from test data file 136. At step 236, a test is performed to compare the maximum permitted deflection at 200 lbs. to the deflection measured to determine if the measured deflection is greater than the permitted deflection. If the answer is "no," then the panel is indicated to "pass" the test at step 238. If the answer is "yes," then the panel is indicated to "fail" the test at step 240.

Suitable logic for the ultimate load test is illustrated in FIG. 13. At step 242, the ultimate load data is retrieved from performance standard data table 134, and at step 244, the measured deflection at ultimate load is retrieved from the test data file 136. At step 246, a test is performed to determine if the panel withstood the ultimate load, in effect, if the measured load at ultimate is greater than just prior to ultimate load, i.e., if the panel breaks under ultimate load, the measured load decreases. If the answer is "yes," then the panel is deemed to have passed the test at step 248; if the answer is "no," then the panel is deemed to have not passed the test at step 250. A report is then printed at step 252 as illustrated in FIG. 14. FIG. 15 is a report wherein the panel tested failed the ultimate load test. The failure is also represented on the graph of load versus deflection wherein the load abruptly decreases as the panel fails under the load.

Security is suitably built into the program by providing unchangeable numbering of the test reports.

The present invention is further explained by the following examples which should not be construed by way of limiting the scope of the present invention.

The following examples show the actual testing of a wood panel in accordance with ASTM E661-88, Standard Test Method for Performance of Wood and Wood-Based Floor and Roof Sheathing Under Concentrated Static and Impact Loads, incorporated herein by reference.

EXAMPLE 1

The present apparatus was operated in accordance with the following specific conditions.

An OSB sample which was subfloor panel and span rated at 16 inches was chosen and placed on the support assembly with the clamp members spaced 16 inches apart from each other. The sample was 24 inches wide and had a thickness of 23/32 inch.

Appropriate data entry for the panel was effected and the program run, and a load applied up to the ultimate load of 400 lbs. (according to Department of Commerce Standard PS-2). For the load deflection test, the actual deflection was read at 201 lbs. to be 0.214 inch. The permitted maximum deflection is 0.250 inch, per PS-2. The panel passed the quality assurance load deflection test.

For the ultimate load test, the program determines if the panel load maintains through the ultimate load, in this case, 400 lbs. It was determined that the panel withstood the ultimate load as evidence by the graph shown in FIG. 14.

EXAMPLE 2

The present apparatus was operated in accordance with the following specific conditions.

An OSB sample which was roofing panel and span rated at 24 inches was chosen and placed on the support assembly with the clamp members spaced 24 inches apart from each other. The sample was 24 inches wide and had a thickness of 7/16 inch.

Appropriate data entry for the panel was effected and the programmed load test was run. The actual deflection was found to be 0.407 inch for a load of 200 lbs. The permitted maximum deflection is 0.469 inch. The panel passed the quality assurance load deflection test.

As described in Example 1, the ultimate load test was run. Similar to Example 1, the ultimate load to be applied to the test panel is 400 lbs. As seen in FIG. 15, the panel failed at a 386-lb. load and hence, failed the test, i.e. measured load decreased after 386 lbs.

In summary, the present invention provides panel performance test system which eliminates the costs and difficulties associated with weekly shipping of products to remote laboratories for testing. The system provides the ability to perform quality control testing in-house, at the mill, for each product run and correct any performance problems virtually immediately. As such, manufacturers have the confidence that their products are meeting quality control standards, and assures the manufacturer's reputation for quality.

While the present invention has now been described and exemplified with some specification, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

I claim:

1. A panel testing system, comprising:
   a support frame, a load-applying assembly, a linear measurement device, and a computer;
   said support frame for supporting and clamping a panel to be tested; said frame comprising (i) a horizontal support section and (ii) a clamping assembly; said horizontal support section supporting said clamping assembly; said clamping assembly for supporting a first major surface of the panel along three spaced apart parallel frame members extending substantially across the width of the panel and clamping against a second opposite major surface of the panel along the three spaced apart parallel frame members extending substantially across the width of the panel;
   said load-applying assembly supported on said support frame for applying a substantially linear standard load to said second major surface of the panel, the standard load being predetermined depending on the end use and span rating of the panel, said load-applying assembly including a load cell for developing and transmitting a load-indicating signal corresponding to the applied load;
   said linear measurement sensor for measuring the magnitude of deflection of the panel under the applied load; said sensor comprising a linear displacement transducer for developing and transmitting a deflection-indicating signal corresponding to the deflection of the panel under the applied load;
   said computer operatively connected to said load cell and said transducer and configured to receive and process said load-indicating signal and said deflection-indication signal into data records of test loads and deflections to determine whether a test deflection is greater than a standard deflection.

2. The system of claim 1, wherein said load-applying assembly is an hydraulically actuated system having an hydraulic ram, a universal joint, a rod, and a loading disk, said ram for applying the load, said load cell contacting said ram, said rod connecting said load cell to said universal joint and said loading disk connected to said universal joint and contacting the panel to be tested.

3. The system of claim 1, wherein said frame includes four upright elongate posts for supporting said horizontal support section and said clamping assembly.

4. The system of claim 1, wherein said clamping assembly includes three substantially C-shaped clamps, each of said clamps having a bottom frame member for supporting said first major surface of the panel and a top portion for clamping against said second major surface of the panel.

5. The system of claim 4, wherein said bottom frame member is an elongate member with a top face and an elongate support bar affixed to said top face.

6. The system of claim 4, wherein said top portion of each said clamp includes an elongate, substantially rectangular bottom surface, a first plate beneath said bottom surface, a second plate beneath said first plate and a hose sandwiched between said first plate and said bottom surface; said second plate coextensive with said first plate and having a flat, substantially rectangular elongate top member and downwardly depending perpendicular member having a plurality of protruding, linearly aligned and spaced apart pins; said hose operatively connected to a pneumatic system for inflating and deflating said hose.

7. The system of claim 1, wherein said computer further processing said test data for printing a report of test results and a graphical representation of applied load versus measured displacement.

8. A load and deflection-measuring system, comprising
   an hydraulic subsystem for applying a load to a panel to be tested;
   a load cell, operatively associated with said hydraulic subsystem, for measuring the applied load;

a linear displacement transducer for measuring a linear deflection of the panel under the applied load;

a computer for storing and executing a program and having a display and at least one input devices, and operatively coupled to said hydraulic subsystem, said load cell and said transducer for recording and processing data relating to said applied load and said deflection, said computer having a central processing unit, a memory medium and data storage means for storing data records, said computer comprising a load/deflection measuring program in execution on said computer for controlling a load/deflection test, said program, operatively communicating with said central processing unit, memory and data storage means, for controlling said applied load, for receiving a load indicating signal from said load cell, for receiving a deflection indicating signal from said transducer, for processing said deflection indicating signal into a deflection value, for comparing said measured deflection value with a standard value, and for determining if the measured deflection is greater than the standard value.

9. The system of claim 8, further comprising a clamping assembly for supporting and clamping the panel; said clamping assembly including three substantially C-shaped clamps, each of said clamps having a bottom frame member for supporting a first major surface of the panel and a top portion for clamping against a second opposite major surface of the panel.

10. The apparatus of claim 8, wherein said program further comprises printing a report of test results and a graphical representation of applied load versus measured displacement.

11. An apparatus for measuring deflection of a panel material under application of a predetermined standard load, comprising:

a first, second and third supports for supporting a panel at spaced apart finite locations;

a load-applying assembly for imparting a load to the panel midway between said first and second supports, said assembly comprising a loading disk and an hydraulic means for applying force to said loading disk;

a load cell operatively connected to said loading disk for measuring the load applied through said loading disk imparted to the panel;

a transducer operatively connected to said load-applying assembly for measuring a displacement of the assembly upon applying force to the panel, said displacement corresponding to a deflection sustained by the panel as a result of the applied load;

a computer for storing and executing a load/deflection measuring program and having a display and at least one user input device, and operatively coupled to said load-applying assembly, said load cell and the transducer for recording and processing data relating to said applied load and said displacement, said computer having a central processing unit, a memory medium and data storage means for storing data records, said load/deflection measuring program in execution on said computer for controlling a load/deflection test, said program, operatively communicating with said central processing unit, memory and data storage means, for controlling the applied load, for receiving a load indicating signal from said load cell, for receiving a displacement indicating signal from said transducer, for processing said displacement indicating signal into a displacement value, for comparing said measured displacement value with a standard value, and for determining if the measured displacement is less than the standard value.

12. A method of testing the performance of a panel under a concentrated load, said method comprising the computer-assisted steps of:

storing in a data table in a memory medium, predetermined standard load and deflection parameters corresponding to end use and span rating of panels;

entering end use and span rating data for a panel to be tested;

determining a predetermined standard ultimate load and standard deflection for a panel to be tested depending upon the end use and span rating of the panel, and testing the performance of the panel upon application of the load;

said testing including:

applying a load to the panel up to the ultimate load, the panel clamped at predetermined span intervals depending upon the span rating of the panel to simulate the fastening of the panel to joists, the load being applied at a point midway between the span intervals measuring the applied load and developing a load-indicating signal corresponding the applied load;

measuring the deflection of the panel upon application of the load and developing a deflection-indicating signal corresponding to said measured deflection;

interpreting said load-indicating signal and said deflection-indicating signal to derive measured test data of applied load and measured deflection, analyzing the measured test data, the predetermined ultimate load and the predetermined standard deflection to determine whether the measured deflection of the panel is greater than the standard deflection;

providing a test result; and printing a report of the test result.

13. A method of testing the performance of a panel under a concentrated load, said method comprising the steps of:

storing in a data table in a memory medium, predetermined standard load and deflection parameters corresponding to end use and span rating of panels;

entering end use and span rating data for a panel to be tested;

supporting a panel to be tested at first, second and third supports spaced apart finite locations;

clamping said panel at said first, second and third supports; said clamping including, for each support, (i) positioning above each support a hose and a plate having a plurality of protruding pins, positioned and secured to the bottom of said hose (ii) inflating and expanding said hose and thereby (iii) displacing downward said plate until said pins contact and penetrate the panel;

determining a predetermined standard load and standard deflection for a panel to be tested depending upon the end use and span rating of the panel, applying a load to the panel midway between said first and second supports via a load-applying assembly, said assembly comprising a loading disk and an hydraulic means for applying force to said loading disk;

measuring the load applied through said loading disk imparted to the panel and developing a load-indicating signal corresponding to the applied load;

measuring a displacement of said assembly upon applying force to the panel, said displacement corresponding to a deflection sustained by the panel as a result of the applied load and developing a deflection-indicating signal corresponding to the measured deflection;

interpreting said load-indicating signal and said deflection-indicating signal to derive test data of measured applied load and measured deflection;

analyzing said measured deflection and said predetermined standard deflection to determine whether the measured deflection of the panel is greater than the standard deflection;

providing a test result; and printing a report of the test result.

* * * * *